United States Patent
Warner et al.

(10) Patent No.: US 9,510,998 B2
(45) Date of Patent: Dec. 6, 2016

(54) FLUID EXCHANGE METHODS AND DEVICES

(71) Applicant: Becton, Dickinson and Company, Franklin Lakes, NJ (US)

(72) Inventors: Brian David Warner, Martinez, CA (US); John Dunne, Livermore, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/755,799

(22) Filed: Jun. 30, 2015

(65) Prior Publication Data

US 2016/0175198 A1 Jun. 23, 2016

Related U.S. Application Data

(62) Division of application No. 14/237,857, filed as application No. PCT/US2012/057997 on Sep. 28, 2012, now Pat. No. 9,095,494.

(Continued)

(51) Int. Cl.
*G01N 15/14* (2006.01)
*A61J 1/20* (2006.01)
(Continued)

(52) U.S. Cl.
CPC .............. *A61J 1/2089* (2013.01); *A61J 1/2003* (2015.05); *A61J 3/00* (2013.01); *A61K 9/0019* (2013.01);
(Continued)

(58) Field of Classification Search
CPC ................................................ G01N 15/1404
See application file for complete search history.

(56) References Cited

U.S. PATENT DOCUMENTS

| 6,929,750 B2 | 8/2005 | Laurell et al. |
| 2003/0031626 A1 | 2/2003 | Rheinlander et al. |

(Continued)

FOREIGN PATENT DOCUMENTS

| WO | 2004033087 A1 | 4/2004 |
| WO | 2007128795 A2 | 11/2007 |

OTHER PUBLICATIONS

Berz et al., "Cryopreservation of hematopoietic stem cells," Am J Hematol 82(6):463-472, 2007.*

(Continued)

*Primary Examiner* — Rosanne Kosson
(74) *Attorney, Agent, or Firm* — Bret E. Field; Bozicevic, Field & Francis LLP

(57) ABSTRACT

Methods and devices for exchanging therapeutic agents, such as cells, from one liquid medium to another liquid medium are provided. Aspects of embodiments of the methods include transferring a therapeutic agent from a first medium, such as a freezing, storage or shipping buffer, into a second medium, such as a sterile physiologically compatible buffer. In certain aspects, the transfer of the therapeutic agent from a first medium to a second medium involves the use of acoustic-focusing, or acoustophoresis. Embodiments of the subject methods may facilitate the transfer of a therapeutic agent from a storage medium to an infusion medium, and in certain embodiments include administering the therapeutic agent contained in the infusion medium to the subject. Also provided by the present disclosure are devices for practicing the subject methods.

20 Claims, 5 Drawing Sheets

Related U.S. Application Data

(60) Provisional application No. 61/541,870, filed on Sep. 30, 2011.

(51) Int. Cl.

| | |
|---|---|
| *A61M 5/14* | (2006.01) |
| *C12N 13/00* | (2006.01) |
| *A61M 1/36* | (2006.01) |
| *A61J 3/00* | (2006.01) |
| *A61K 9/00* | (2006.01) |
| *A61M 5/19* | (2006.01) |
| *B65B 3/00* | (2006.01) |
| *A61M 37/00* | (2006.01) |

(52) U.S. Cl.
CPC ......... *A61M 1/3678* (2014.02); *A61M 1/3693* (2013.01); *A61M 5/1407* (2013.01); *A61M 5/1413* (2013.01); *A61M 5/19* (2013.01); *B65B 3/003* (2013.01); *C12N 13/00* (2013.01); *A61M 37/00* (2013.01); *A61M 2205/10* (2013.01)

(56) References Cited

U.S. PATENT DOCUMENTS

| | | |
|---|---|---|
| 2010/0317093 A1 | 12/2010 | Turewicz et al. |
| 2011/0208113 A1 | 8/2011 | Toma et al. |

OTHER PUBLICATIONS

Augustsson et al., "Decomplexing biofluids using microchip based acoustophoresis", Lab on a Chip, vol. 9, pp. 810-818 (2009).

Bakken, "Cryopreserving Human Peripheral Blood Progenitor Cells", Current Stem Cell Research & Therapy, vol. 1, pp. 47-54 (2006).

Berz et al.,"Cryopreservation of Hematopoietic Stem Cells", Am J Hematol., vol. 82, No. 6, pp. 463-472 (2007).

Dykes et al., "Efficient Removal of Platelets from Peripheral Blood Progenitor Cell Products Using a Novel Micro-Chip Based Acoustophoretic Platform", Plos One, vol. 6, No. 8, pp. 1-10 (2011).

Jonsson et al., "Particle Separation Using Ultrasound Can Radically Reduce Embolic Load to Brain After Cardiac Surgery", vol. 78, Ann Thorac Surg, pp. 1572-1578 (2004).

Laurell, "Acoustophoresis—A Sound Approach to Chip Based Cell Handling", 15th International Conference on Miniaturized Systems for Chemistry and Life Sciences, pp. 1379-1381 (2011).

Laurell et al., "Chip integrated strategies for acoustic separation and manipulation of cells and particles", Chemical Society Reviews, vol. 36, pp. 492-506 (2007).

Petersson et al., "Carrier Medium Exchange through Ultrasonic Particle Switching in Microfluidic Channels", Anal. Chem., vol. 77, pp. 1216-1221 (2005).

Petersson et al., "Free Flow Acoustophoresis: Microfluidic-Based Mode of Particle and Cell Separation", Analytical Chemistry, vol. 79, No. 14, pp. 5117-5123 (2007).

Suzuki et al., "Acute Blood Purification", Contrib. Nephrol., vol. 166, (2010).

Augustsson et al. "Buffer medium exchange in continuous cell and particle streams using ultrasonic standing wave focusing", Microchim Acta, vol. 164, No. 3-4, Jul. 18, 2008, pp. 269-277.

Extended European Search Report issued Apr. 23, 2015 in related European Application No. 12835543.5, 10 pages.

Glass et al. "Optimization of a microfluidic device for diffusion-based extraction of DMSO from a cell suspension," International Journal of Heat and Mass Transfer 51 (2008) 5749-5757.

\* cited by examiner

FLUID EXCHANGE METHODS AND DEVICES

CROSS-REFERENCE TO RELATED APPLICATIONS

Pursuant to 35 U.S.C. §119 (e), this application is a divisional application of U.S. patent application Ser. No. 14/237,857, filed Feb. 7, 2014, which application is a 371 national phase filing of International Application No. PCT/US2012/057997, filed Sep. 28, 2012, which application claims priority to the filing date of the U.S. Provisional Patent Application Ser. No. 61/541,870, filed Sep. 30, 2011, the disclosures of which are incorporated herein by reference.

INTRODUCTION

High-dose chemotherapy followed by autologous peripheral blood stem cell (PBSC) transplantation is used for many hematological malignancies. PBSCs are often mobilized from the bone marrow with cytokines such as recombinant G-CSF (rhuG-CSF) and then cryopreserved. This process requires the addition of cryopreservatives such as dimethyl sulphoxide (DMSO) to prevent cell lysis during freezing. The occurrence of adverse events during the infusion of previously cryopreserved autologous PBSC is known, and has traditionally been attributed to the presence of DMSO in the thawed cell suspension.

Cryopreserved cell preparations containing DMSO can be washed prior to infusion. Typically, such cell preparations are washed by centrifugation-based methods. Centrifugation-based methods have disadvantages related to batch processing with manual steps that are error-prone, incomplete fluid exchange, hypoxia in the pelleting of live cells, and incomplete re-suspension of the pelleted particles. Such processes typically require mechanical devices with power requirements inconvenient for routine bedside use in a clinical setting.

Alternatively, cell preparations can be washed by filtration carried out using a porous membrane to separate fluid and small particles from larger particles, e.g., the cells to be transplanted. Limitations of filtration methods are well known, and include clogging of the membrane as large particles accumulate, which can change the fluid dynamics in a poorly controlled way, limit the purity of the desired particles by trapping undesired particles as the pore size of the membrane is effectively changed by accumulation of large particles, and damage the large particles by aggregating them under increasing fluid pressure and shear and hypoxia associated with clumping of living cells. The large particles can be difficult to recover and the process is usually restricted to batch processing with incomplete fluid transfer.

SUMMARY

Methods and devices for exchanging therapeutic agents, such as cells, from one liquid medium to another liquid medium are provided. Aspects of embodiments of the methods include transferring a therapeutic agent from a first medium, such as a freezing, storage or shipping buffer, into a second medium, such as a sterile physiologically compatible buffer. In certain aspects, the transfer of the therapeutic agent from a first medium to a second medium involves the use of acoustic-focusing, or acoustophoresis. Embodiments of the subject methods facilitate the transfer of a therapeutic agent from a storage medium to an infusion medium, and in certain embodiments include administering the therapeutic agent contained in the infusion medium to a subject. Also provided are devices and kits that find use in practicing embodiments of the methods, e.g., as described below.

In certain embodiments, methods of the present disclosure involve the use of acoustophoresis to transfer a therapeutic agent from a first medium, such as a freezing, storage or shipping buffer, into a second medium. Such acoustophoresis may include the use of one or more acoustophoresis devices, such as 2 or more, including 5 or more, 10 or more, or 20 or more. A range of acoustophoresis devices may be used in practicing the subject methods, varying in some embodiments in terms of scale (e.g., macro- or micro-scale acoustophoresis); chip material (e.g., silicon, glass, etc.); chip dimensions; number of separation channels (e.g., 1 or more, 2 or more, 5 or more, 10 or more, 20 or more, etc.); orientation of the separation channels (e.g., serial, parallel, and/or both); dimensions of the separation channel(s); number of inputs and outputs; type of vibration generator (e.g., a piezoceramic transducer, such as lead zirconate titanate (PZT)); number of vibration generators; frequency and/or voltage applied to the vibration generator; flow rate (e.g., about 1 µl/min, about 100 µl/min, about 1 ml/min, or about 100 ml/min or more); presence or absence of pumps or valves (e.g., one or more syringe pumps, elastomeric pumps, and/or peristaltic pumps); and the like, as shall be described more fully herein. In certain aspects, acoustophoresis includes gravimetric fluid flow, and/or mechanically-assisted fluid flow (e.g., using a pump, such as a syringe pump or a peristaltic pump).

Further, acoustophoresis devices of interest include, but are not limited to, devices as described in U.S. Pat. No. 6,929,750; Laurell, et al. (2007) Chem. Soc. Rev., 2007, 36, 492-506; Petersson, et al. (2005) Analytical Chemistry 77: 1216-1221; and Augustsson, et al. (2009) Lab on a Chip 9: 810-818; the disclosures of which are incorporated herein by reference.

A broad range of therapeutic agents may be transferred from one fluid medium to another by using methods of the present disclosure. In certain aspects, a therapeutic agent is a cell, such as a peripheral blood stem cell (PBSC), umbilical cord blood cell, hematopoietic stem cell, or induced pluripotent stem cell. Therapeutic agents of interest further include, but are not limited to, drugs, nucleic acids, protein therapeutics (e.g., antibodies, such as monoclonal antibodies; and peptides), blood and blood products, and chemotherapy agents. In certain embodiments, a therapeutic agent is contained within or coupled to a particle, carrier, vesicle, or other delivery device, such as a bead or a liposome. Therapeutic agents of interest include agents of biological origin, including agents obtained from an in vivo source (e.g., a mammalian subject, a human subject, etc.), as well as agents of non-biological origin (e.g., chemical or synthetic origin).

In certain aspects, a therapeutic agent is transferred from one medium to a different type of medium, such as from a freezing, storage or shipping buffer, into a sterile physiologically compatible buffer. Aspects may also, or instead, include transferring a therapeutic agent from a medium into the same type of medium. In certain aspects, transferring the therapeutic agent to a different medium may have the effect of removing one or more components from the environment in which the therapeutic agent is present, such as cryopreservatives (e.g., DMSO, glycerol), density gradient reagents (e.g., Ficoll), enzymes (e.g., collagenase), lysing reagents (e.g., red cell lysing reagents), antibodies, lipids, etc.

In certain embodiments, the therapeutic agent is administered to a subject, such as by infusion. Administration of a therapeutic agent to a subject may be achieved in various ways, including, but not limited to, oral, parenteral (e.g., subcutaneous, intramuscular, intradermal, intravenous and intrathecal), intraperitoneal, intravesicular, etc., administration. Subjects suitable for the methods of the present disclosure include mammals (e.g., humans). Aspects of the methods include allotransplantation, xenotransplantation, or self-transplantation. In certain aspects, the methods are performed under sterile conditions and/or are sterile.

Also provided by the present disclosure are devices for practicing the subject methods. In certain embodiments, devices may include a first container providing a therapeutic agent suspended in a first medium, a second container providing a second medium, and an acoustophoresis device in fluid communication with the first and second containers and configured to transfer the therapeutic agent from the first medium into the second medium.

Devices of the present disclosure may include one or more processors configured to control the device. In certain aspects, a processor may be configured to control an acoustophoresis device, such as by altering one or more of the flow rare (e.g., by controlling one or more pumps), the shape, frequency end/or power of the electrical energy delivered to the vibration generator. Aspects of the present disclosure further include closed-loop devices.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
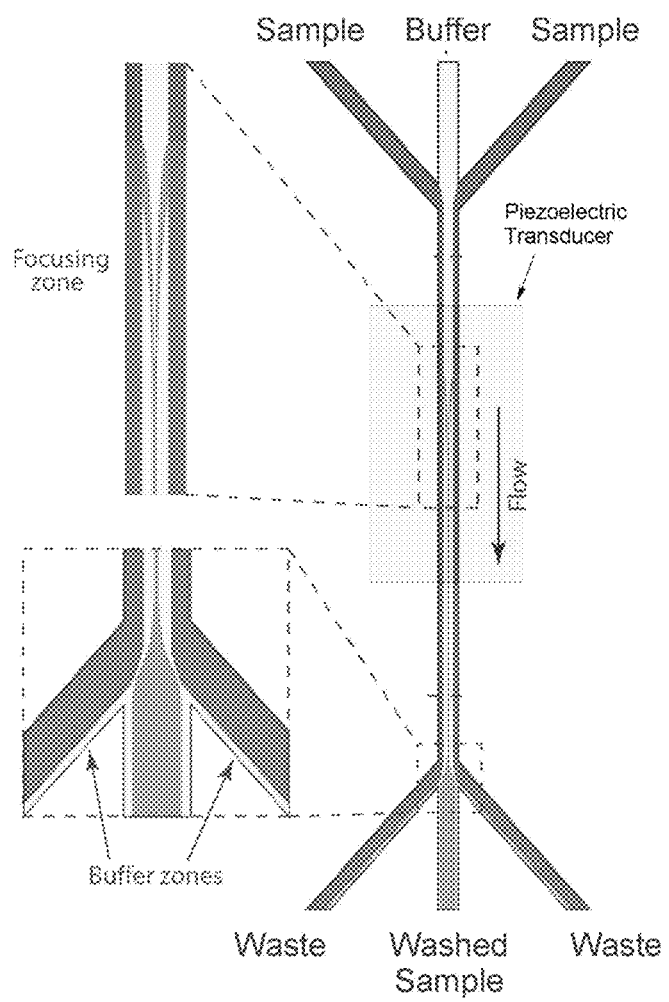
FIG. 1 provides a schematic depiction of a microfluidic acoustophoresis device that allows for the transfer of a therapeutic agent (e.g., cells) from a first medium into a second medium by acoustic focusing.

Methods and devices for exchanging therapeutic agents, such as cells, from one liquid medium to another liquid medium, are provided. Aspects of embodiments of the methods include transferring a therapeutic agent from a first medium, such as a freezing, storage or shipping buffer, into a second medium, such as a sterile physiologically compatible buffer. In certain aspects, the transfer of the therapeutic agent from a first medium to a second medium involves the use of acoustophoresis. Embodiments of the subject methods facilitate the transfer of a therapeutic agent from a storage medium to an infusion medium, and in certain embodiments include administering the therapeutic agent contained in the infusion medium to the subject. Also provided by the present disclosure are devices for practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As described above, the present disclosure provides methods for exchanging therapeutic agents, such as cells, from one liquid medium to another liquid medium. Aspects of embodiments of the methods include transferring a therapeutic agent from a first medium into a second medium. In certain aspects, the transfer of the therapeutic agent from a first medium to a second medium involves the use of acoustophoresis. Embodiments of the subject methods facilitate the transfer of a therapeutic agent from a storage medium to an infusion medium, and in certain embodiments include administering the therapeutic agent contained in the infusion medium to the subject.

Various steps and aspects of the methods shall now be described in greater detail below.

Therapeutic Agents

As used, herein, the term "therapeutic agent" means any agent that may have a biological function and/or therapeutic effect in a subject. For example, a therapeutic agent may be one or more cells (e.g., stem cells, such as PBSCs, umbilical cord blood cells, hematopoietic stem cells, induced pluripotent stem cells, and the like). Examples of such therapeutic agents include, but are not limited to, approved cell therapy products (e.g., U.S. Food and Drug Administration approved cell therapy products) including HemaCord (hematopoietic progenitor cells, cord blood; distributed by New York Blood Center Inc., New York, N.Y.); Provenge (Sipuleucel-T; distributed by Dendreon Corporation, Seattle, Wash.); and Laviv (Azficel-T; distributed by Fibrocell Technologies, Exton, Pa.). Therapeutic agents of interest further include, but are not limited to, protein therapeutics (e.g., antibodies, such as monoclonal antibodies; and peptides), blood and blood products, and chemotherapy agents.

In some instances, a therapeutic agent to be transferred has a diameter of about 0.25 micron or greater, such as 1 micron or greater, including about 1 to 10 microns, about 10 to 20 microns, about 20 to 30 microns, about 30 to 40 microns, about 40 to 50 microns, about 50 to 60 microns, about 60 to 70 microns, about 70 to 80 microns, about 80 to 90 microns, about 90 to 100 microns, about 100 to 125 microns, about 125 to 150 microns, or about 150 microns or more.

Further, in some instances the therapeutic agent to be transferred has a density greater than at least one of the medium in which it is contained and the medium into which it is being transferred. In certain aspects, the therapeutic agent to be transferred has a compressibility greater than at least one of the medium in which it is contained and the medium into which it is being transferred.

In certain aspects, an isolated therapeutic agent has a size, density, and/or compressibility not amenable to transfer by acoustophoresis and is instead contained within, associated with, or coupled to a particle to facilitate acoustophoresis of the therapeutic agent. In certain aspects, the particle has a size, density, and/or compressibility amenable to acoustophoresis. Aspects of the subject methods include preparing a therapeutic agent so that it is contained within, associated with, or coupled to a particle to facilitate acoustophoresis of the therapeutic agent. Any convenient particle amenable to acoustophoresis to which a therapeutic agent may be associated (e.g., covalently and/or non-covalently, directly and/or indirectly, etc.) may be employed in practicing the subject methods.

Particles of interest include vesicles, such as liposomes. Liposomes amenable to transfer by acoustophoresis and comprising a therapeutic agent may be made using any convenient method and material. The therapeutic agent may be contained in the aqueous interior of the liposome and/or associated with a surface, e.g., interior or exterior, of the liposome. As such, in certain aspects, the therapeutic agent is also, or instead, contained on the exterior surface of the liposome or within the lipid bilayer of the liposome.

In some embodiments, the particle is a bead (e.g., a polymer bead) to which the therapeutic agent is attached. A therapeutic agent may be attached to a bead directly (e.g., covalently or non-covalently) or indirectly (e.g., with one or more binding intermediates, to which the therapeutic agent is covalently or non-covalently attached). Methods of manufacturing beads and attaching therapeutic agents are known in the art.

Accordingly, a broad range of therapeutic agents may be used in practicing the subject methods, including drugs, nucleic acids, etc. In certain aspects, a therapeutic agent is a therapeutic protein, such as a therapeutic protein contained within a liposome. Therapeutic proteins of interest include, but are not limited to, proteases, protease inhibitors, cytokines, chemokines, gonatotrophins, chemoactins, lipid-binding proteins, pituitary hormones, growth factors, somatomedians, immunoglobulins, interleukins, sex hormone binding globulin, interferons, growth hormone releasing hormone, parathyroid hormone, calcitonin, leuprolide, insulin-like growth factor-1 and scaffolding proteins such as DARPINs, knottins, FN3 domains, CH domains, Elastin-like polypeptides, and cyclic polypeptides, such as CYCLOTIDEs. Therapeutic proteins of interest include antibodies (e.g., a humanized antibody) and antigen fragments thereof.

Therapeutic agents of interest include agents obtained from an in vitro source (e.g., laboratory cells grown in culture), from an in vivo source (e.g., a mammalian subject, a human subject, etc.), or from a non-biological source (e.g., synthetic and/or chemical source). In some embodiments, a therapeutic agent is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the therapeutic agent is obtained from an in vivo source, including agents obtained from tissues (e.g., a tissue biopsy, cell suspension from a tissue sample, etc.) and/or body fluids (e.g., whole blood, fractionated blood, plasma, serum, saliva, lymphatic fluid, interstitial fluid, etc.). In some cases, a therapeutic agent derived from a subject is cultured, stored (e.g., cryopreserved), or manipulated prior to practicing the subject methods.

In certain embodiments the source of the therapeutic agent is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the source of the therapeutic agent is human.

Media

A therapeutic agent may be contained in a medium. For instance, a therapeutic agent may be contained in suspension at any desired concentration. For example, where the therapeutic agent is a cell, the medium can contain $10^{11}$ or less, $10^{10}$ or less, $10^9$ or less, $10^8$ or less, $10^7$ or less, $10^6$ or less, $10^5$ or less, $10^4$ or less, $10^3$ or less, 500 or less, 100 or less, 10 or less, or one cell per milliliter. Any convenient media may be used in practicing the subject methods, including, but not limited to, freezing buffers, storage buffers, shipping buffers, physiologically compatible buffers, sterile buffers, and the like. In some instances, the medium into which a therapeutic agent is being transferred has a higher density than does the medium in which the therapeutic agent is contained.

In certain aspects, a medium may include one or more solutes in addition to the therapeutic agent. For instance, a medium may also include one or more cryopreservatives (e.g., DMSO, glycerol, propylene glycol, hydroxyethyl starch), density gradient reagents (e.g., Ficoll), enzymes (e.g., collagenase), lysing reagents (e.g., red cell lysing reagents), antibodies, lipids, etc. In other aspects, the medium may contain no solutes other than the therapeutic agent.

Embodiments of the subject methods include media containing two or more different therapeutic agents, including 3 or more, such as 4 or more, 5 or more, 6 or more, 7 or more, 8 or more, 9 or more, or 10 or more. The different therapeutic agents may differ in any respect from one another, such as the type (e.g., cell vs. protein therapeutic), sub-type (e.g., PBMCs vs. umbilical cord blood cells), etc.

Aspects of embodiments of the subject methods include transferring a therapeutic agent from one medium (e.g., a first medium) into another medium (e.g., a second medium). In certain aspects, a therapeutic agent may be subsequently transferred from the second medium to a third, fourth, fifth, etc., medium. For instance, in certain embodiments a therapeutic agent may be transferred from a first medium into a second medium, and subsequently transferred from the second medium into a third medium, and subsequently transferred from the third medium to a fourth medium, etc.

The medium into which a therapeutic agent is transferred may be the same type or a different type of medium compared with the medium from which the therapeutic agent is being transferred. In certain aspects, the medium is the same type (e.g., both the first medium and the second medium are physiologically compatible buffers). In other aspects, the media are of different types, such as the first medium is a freezing buffer and the second (or third, fourth, etc.) medium is a physiologically compatible buffer. Any convenient media into which a therapeutic agent may be transferred may be used.

In certain aspects, the first medium is a freezing buffer. In certain aspects, a freezing buffer is a medium containing one or more cryoprotective agents, such as DMSO, glycerol, propylene glycol, etc. The freezing buffer may facilitate the freezing (e.g., cryopreservation) of a therapeutic agent, such as cells. In certain aspects, the freezing buffer may be thawed prior to or in conjunction with practicing the subject methods, using any convenient thawing method known in the art. Examples of freezing buffers of interest include, but are not limited to, Recovery™ cell culture freezing medium (Life Technologies Corporation, Carlsbad, Calif.); Synth-a-Freeze® cryopreservation medium (Life Technologies Corporation, Carlsbad, Calif.); CPZ™ cryopreservation media (INCELL Corporation, San Antonio, Tex.); EZ-CPZ™ cryopreservation media (INCELL Corporation, San Antonio, Tex.); Cell Freezing Medium-I freezing buffer (Atlanta Biologicals, Lawrenceville, Ga.); Cell Freezing Medium-II freezing buffer (Atlanta Biologicals, Lawrenceville, Ga.); and CryoStor® cell cryopreservation media (Sigma-Aldrich, St. Louis, Mo.).

Embodiments include a first medium having a concentration of cryoprotectant of 1% (v/v) or more, including about 2% (v/v) to about 5% (v/v), about 2% (v/v) to about 5% (v/v), about 5% (v/v) to about 7.5% (v/v), about 7.5% (v/v) to about 10% (v/v), about 10% (v/v) to about 15% (v/v), about 20% (v/v) to about 25% (v/v), or about 25% (v/v) to about 30% (v/v). Two or more cryoprotectants, such as 3 or more, including 4 or more, 5 or more, 6 or more, or 7 to 10, may be present in a first media. Where two or more cryoprotectants are present in a medium, the cryoprotectants may be present at the same concentration (e.g., 5% DMSO and 5% HES) or different concentrations (e.g., 5% DMSO and 6% HES).

In certain embodiments, a buffer may be contained within a container, such as a cryocontainer. Containers of interest include containers that are Ethinyl Vinyl Acetate (EVA) based, and containers that are not EVA based (e.g., Teflon, Kaplon, FEP/Polyimide, stainless steel, and the like). In certain aspects, the container is an EVA freezing bag, such as a Cryocyte™ freezing bag (Baxter Healthcare Corporation, Deerfield, Ill.), Cell-Freeze® cryogenic freezing bag (Charter Medical, Winston-Salem, N.C.), OriGen Cryostore™ freezing bag (OriGen BioMedical, Austin, Tex.), and the like.

Embodiments of the subject methods include transferring a therapeutic agent to a physiologically compatible buffer. Examples of physiologically compatible buffers of interest include, but are not limited to, electrolyte solutions approved for infusion and/or injection into human subjects (e.g., U.S. Food and Drug Administration approved electrolyte injection solutions). In certain aspects, the physiologically compatible buffer is sterile. Examples of physiologically compatible buffers of interest include, but are not limited to, dextrose monohydrate injection solution (e.g., 5% Dextrose Injection, such as that distributed by Hospira Inc., Lake Forest, Ill.), Lactated Ringer's Injection solution (Hospira Inc., Lake Forest, Ill.), PLASMA-LYTE solutions (Baxter Healthcare Corporation, Deerfield, Ill.); and Isolyte® S solutions (B. Braun Medical Inc., Ontario, Canada).

Acoustophoresis Devices

Transferring a therapeutic agent from one medium into another medium may include the use of an acoustophoresis device. As used herein, the terms "acoustic-focusing device" and "acoustophoresis device" are used broadly and generically to refer to a device in which particulate matter in a fluid may be controlled or manipulated by means of ultrasonic standing waves, and the terms may be used interchangeably. Examples of acoustophoresis devices of interest include, but are not limited to, those described in U.S. Pat. No. 6,929,750; Laurell, et al. (2007) Chem. Soc. Rev., 2007, 36, 492-506; Petersson, et al. (2005) Analytical Chemistry 77: 1216-1221; and Augustsson, et al. (2009) Lab on a Chip 9: 810-818; the disclosures of which are incorporated herein by reference.

FIG. 1 a schematic depiction of a microfluidic acoustophoresis device that allows for the transfer of a therapeutic agent from a first medium into a second medium by acoustic focusing. In this example, the direction of fluid flow is from the top to the bottom of the figure. The acoustophoresis device includes two sample inlets and a buffer inlet. With the inputs arranged as illustrated, the sample fluid (dark gray; corresponding to a first medium comprising a therapeutic agent) flows along the sides of the channel, with the buffer (light gray; corresponding to a second medium) flowing between, with the fluids operating under laminar flow. As such, the first liquid medium and the second liquid medium are combined in a manner sufficient to produce a laminar flow of the first and second media, i.e., a flow in which the two media are flowing in distinct but adjacent and contacting flow paths. The densities of the first and second media differ in some instances in order to ensure the production of the laminar flow upon combination, where in some instances the density difference between the first and second media is 1% or greater, such as 5% or greater, including 10% or greater. A piezoelectric transducer is located below the channel which, when activated, creates an acoustic standing wave in the channel. The acoustic standing wave causes certain particles contained in the samples to move from the sides of the channel in the first media towards the pressure node formed in the center of the channel (as indicated by the focusing zone; top inset) in the second media. These particles (e.g., the therapeutic agent), now contained in buffer (that is, the second medium), are collected by the washed sample outlet. Two outlets placed at the sides of the channel collect waste.

Figure 2:
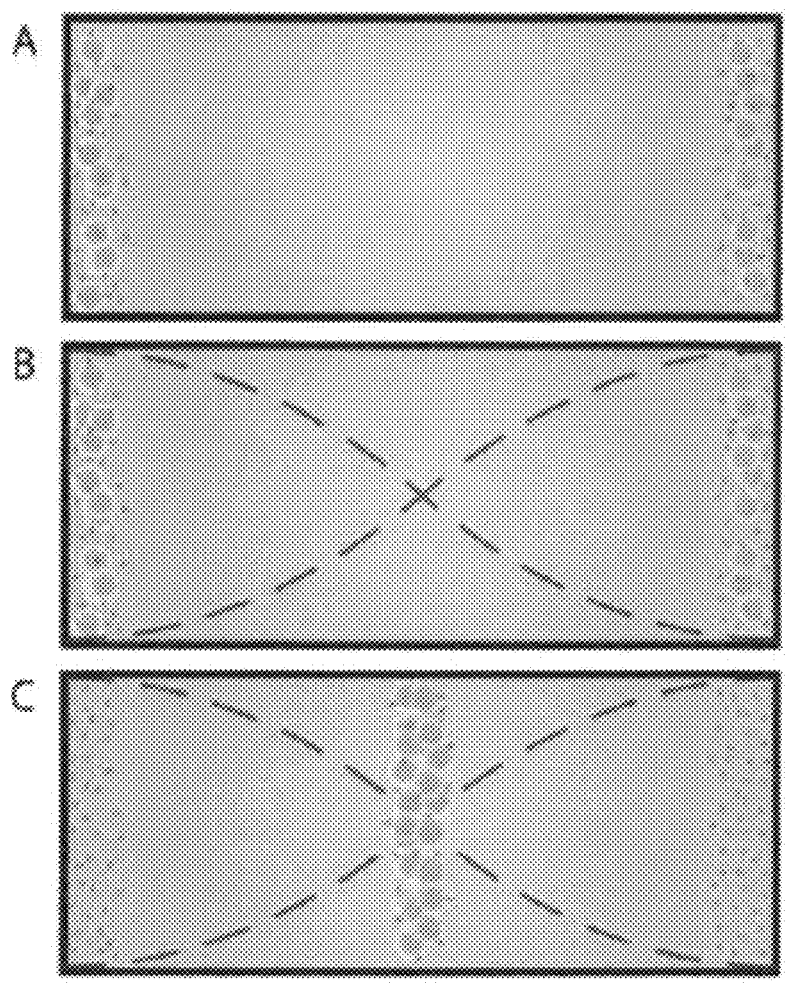
FIG. 2, Panels A-C provide cross-section illustrations of a separation channel of an acoustophoresis device. Particles begin by flowing along the sides of the channel (Panel A). An acoustic standing wave may be induced in the channel (e.g., using a vibration generator, such as a piezoelectric transducer, placed adjacent to the channel), as indicated by the dashed lines (Panels B-C). The acoustic standing wave creates a pressure node in the center of the channel (Panel B). Particles present in the channel may move towards the pressure node (Panel C).

General principles of certain aspects of acoustophoresis devices are illustrated in FIG. 2, Panels A-C, which provide cross-section illustrations of an acoustophoresis separator channel. As depicted in these panels, particles begin by flowing along the sides of the channel (FIG. 2, Panel A). An acoustic standing wave may be induced in the channel (e.g., using a vibration generator, such as a piezoelectric transducer, placed adjacent to the channel), as indicated by the dashed lines (FIG. 2, Panels B-C). The acoustic standing wave creates a pressure node in the center of the channel (FIG. 2, Panel B). Certain particles present in the channel may move towards the pressure node (FIG. 2, Panel C), depending upon their physical properties. Generally, molecules and particles smaller than about 1 micron in diameter are not affected by the acoustic standing wave(s).

The mechanism by which acoustophoresis devices operate is described in, for example, Laurell, et al. (2007) Chem. Soc. Rev., 2007, 36, 492-506. Briefly, an acoustic contrast factor (also called a Φ-factor) depends on both a particle's (e.g., a cell) density ($\rho_c$) and its compressibility ($\beta_c$) in relation to the corresponding properties of the surrounding medium ($\rho_w$, $\beta_w$). An acoustic contrast factor may be positive or negative, which determines the direction of the acoustic force and whether a particular particle will move towards a standing pressure wave node (i.e., the center of the image in FIG. 2, Panel B) or towards the pressure antinode (i.e., the sides of the channel in FIG. 2, Panel B). Generally, solid particles in aqueous media are moved towards a pressure node. Accordingly, depending on the application, the shape and dimensions of the channel(s), the materials from which the acoustophoresis device channel is made, the number of inlets and outlets employed, the flow rate in the channel, the frequency of ultrasound applied, and other parameters of an acoustophoresis device may vary.

In certain aspects, an acoustophoresis device may be based upon the Lund-method, in which acoustic concentration or separation of suspended particles is based on a laminar flow microchannel that is ultrasonically actuated from below using a vibration generator, such as a piezoelectric ceramic. The width of the channel may be chosen to correspond to half the desired ultrasonic wavelength, thereby creating a resonator between the side walls of the flow channel in which a standing wave can be formed. The induced standing wave may thus be generated orthogonal to the incident ultrasonic wave front. As suspended particles with a positive Φ-factor perfuse the channel they are moved, by means of the axial primary radiation force (PRF), towards the pressure nodal plane along the channel center, while those with a negative Φ-factor are moved towards the anti-nodal planes dose to the side wads (FIG. 2, Panel C). The end of the separation channel is split into three or more outlet channels, thus allowing the positive Φ-factor particles to exit through a center outlet and the negative Φ-factor particles to exit through side outlets (FIG. 1).

Figure 3:
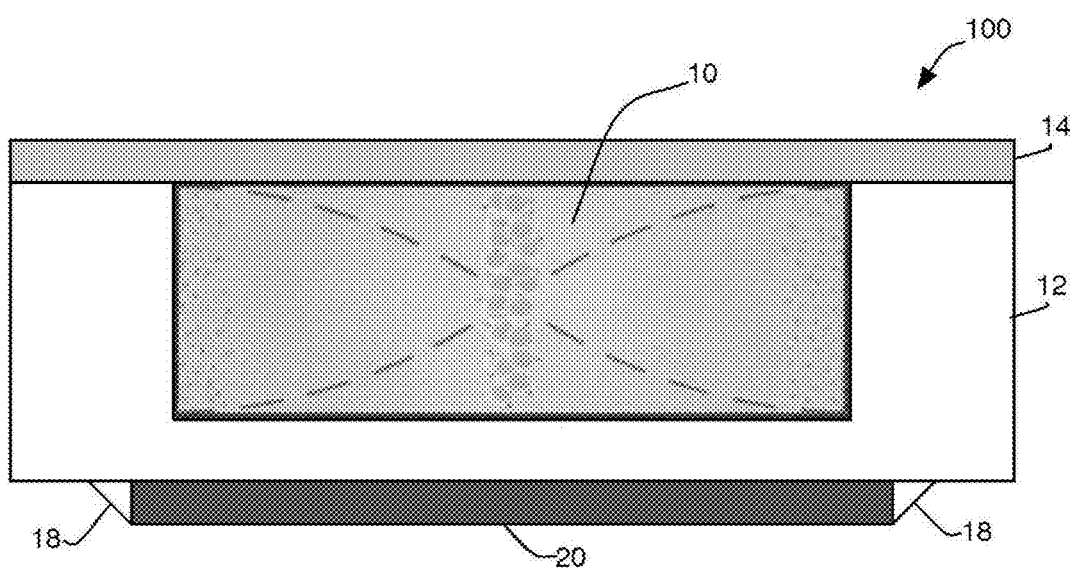
FIG. 3 provides a schematic cross-section of an acoustophoresis separator chip. In this embodiment, the separator chip 100 includes a chip 12 in which a channel 10 has been formed, such as by etching. A membrane 14 (e.g., a glass membrane, such as boron silica glass) is attached to the top of the chip 12. A vibration transducer 20 is affixed to the bottom of the chip 12, using affixing means 18 (e.g., adhesives, gels, and the like).

An example of an embodiment in which an acoustophoresis device of the present disclosure is based upon the Lund-method is shown in FIG. 3, which provides a schematic cross-section of an acoustophoresis separator chip. In this embodiment, the separator chip 100 includes a chip 12 in which a channel 10 has been formed, such as by etching. A membrane 14 (e.g., a glass membrane, such as boron silica glass) is attached to the top of the chip 12. A vibration transducer 20 is affixed to the bottom of the chip 12, using affixing means 18 (e.g., adhesives, gels, and the like). In some embodiments, affixing means 18 may involve gluing the vibration transducer 20 to the chip 12, or using a fluid such as glycerol to couple the acoustic energy of the vibration transducer 20 to the channel 10 contained within the chip 12.

Acoustophoresis devices, such as the separator chip 100 depicted in FIG. 3, may be manufactured from any convenient material. In certain embodiments, the material has is a high Q-value material (i.e., transmits sound waves at low losses) that displays good acoustic reflection properties when the sound wave transits from the fluidic media into the boundary wall, and/or the material may offer a low temperature rise (e.g., silicon). In certain aspects, one or more flow channels 10 are made by etching (e.g., anisotropically etching) a channel in silicon, glass (e.g., Pyrex glass), steel, Poly(methyl methacrylate), polycarbonate, or any other convenient material. The channel(s) may be sealed using a membrane 14 sealed atop the channel. Any convenient membrane type may be used, such as glass (e.g., boron silica glass). In certain aspects, a vibration generator 20 is bonded to the bottom of the channel, Vibration generators of interest include, but are not limited to, piezoelectric transducers such as PZT. In certain aspects, the piezoelectric transducer is of the multi-layer type, but a bimorph piezoelectric element may also be used as well as any other kind of ultrasound generating element with suitable dimensions.

In certain aspects, the dimensions for a channel in which to perform acoustic focusing are about 375 μm×about 150 μm×about 30-70 mm. In other aspects, the channel may vary, for example from about 100-550 μm×about 50-250 μm×about 20-100 mm. In certain aspects, the width of the channel may be chosen to correspond to half the desired ultrasonic wavelength, thereby creating a resonator between the side walls of the flow channel in which a standing wave can be formed. The resonant frequency of the channel may, in certain embodiments, depend on the width of the channel, the speed of sound in the liquid medium or media passing through the chip, and/or other factors known in the art.

In certain embodiments, the frequency of the acoustic wave that is applied corresponds to the fundamental resonance mode of the vibration transducer (e.g., about 2 MHz for many PZT plates) and/or is dependent upon the resonant frequency of the channel (e.g., as described above). The frequency may, in some embodiments, correspond to a harmonic of the vibration transducer, such as a first harmonic, second harmonic, and the like. In various aspects, the frequency applied may be about 1.5 MHz or more, including about 1.9 MHz or more, e.g. about 2.0 MHz to about 2.15 MHz or more, such as about 2.0 MHz to about 2.1 MHz, about 2.1 to about 2.2 MHz, about 2.2 MHz to about 2.3 MHz, about 2.3 to about 2.4 MHz, about 2.5 MHz to about 3.0 MHz, about 3.0 MHz to about 3.5 MHz, about 3.5 to about 4.0 MHz, about 4.0 MHz to about 5.0 MHz, or about 5.0 MHz to 10.0 MHz.

The activation voltage that is applied may also vary. For example, in certain aspects an activation voltage is about 0.1 $V_{pp}$ to about 100 $V_{pp}$, such as about 0.1 $V_{pp}$ to about 1 $V_{pp}$, about 1 $V_{pp}$ to about 10 $V_{pp}$, about 10 $V_{pp}$ to about 20 $V_{pp}$, about 20 $V_{pp}$ to about 30 $V_{pp}$, about 30 $V_{pp}$ to about 40 $V_{pp}$, about 40 $V_{pp}$ to about 50 $V_{pp}$, about 50 $V_{pp}$ to about 75 $V_{pp}$, about 75 $V_{pp}$ to about 100 $V_{pp}$.

In certain embodiments, the acoustophoresis device may include one or more cooling elements (e.g., a Peltier element, heatsink, heat pipe, cooling fan, and the like) to cool the vibration transducer and/or to avoid excessive heating of the therapeutic agents or media. For example, in certain aspects the activation voltage is about 25-30 30 $V_{pp}$ or higher, and the acoustophoresis device contains one or more cooling elements configured to keep the temperature of the vibration transducer below a given value (e.g., about 40° C. or less, such as about 37° C.).

In certain aspects, an acoustophoresis device may be controlled by a processor configured to control the vibration generator. The processor may be contained within a control unit or control box. In certain aspects, the processor is configured to control the vibration generator by altering one or more of the shape, frequency and power of the electrical energy delivered to the vibration generator.

The flow rate of an acoustophoresis device may vary. In certain embodiments, the flow rate of the acoustophoresis device is adjusted such that the output from the acoustophoresis device is optimal for subsequent analysis, such as sorting on a flow cytometer. In other aspects, the flow rate of the acoustophoresis device is adjusted such that the output from the acoustophoresis device facilitates administration of the therapeutic agent to a subject.

In certain aspects, the rate at which one or more acoustophoresis devices exchange a therapeutic agent contained in a first medium into a second medium is about 1 μl/min or more. For example, in certain aspects the rate is about 10 μl/min to 1 L/min, including about 10 μl/min to about 50 μl/min, about 50 μl/min to about 100 μl/min, about 100 μl/min to about 200 μl/min, about 200 μl/min to about 300 μl/min, about 300 μl/min to about 400 μl/min, about 400 μl/min to about 500 μl/min, about 500 μl/min to about 600 μl/min, about 600 μl/min to about 700 μl/min, about 700 μl/min to about 800 μl/min, about 800 μl/min to about 900 μl/min, about 900 μl/min to about 1 ml/min, about 1 ml/min to about 10 ml/min, about 10 ml/min to about 20 ml/min, about 20 ml/min to about 30 ml/min, about 30 ml/min to about 40 ml/min, about 40 ml/min to about 50 ml/min, about 50 ml/min to about 60 ml/min, about 60 ml/min to about 70 ml/min, about 70 ml/min to about 80 ml/min, about 80 ml/min to about 90 ml/min, about 90 ml/min to about 100 ml/min, about 100 ml/min to about 150 ml/min, about 150 ml/min to about 200 ml/min, about 200 ml/min to about 500 ml/min, or about 500 ml/min to 1 L/min.

In certain aspects, the flow rate may be controlled by modulating one or more pumps (e.g., a syringe pump, such as a WPI sp210iwz distributed by World Precision Instruments Inc., Sarasota, Fla.; elastomeric pumps; and/or peristaltic pumps) or valves (e.g., pinch valves). The flow rate may, in certain embodiments, be controlled by a processor, such as a processor described above. In other aspects, the flow rate may be determined by gravimetric fluid flow.

In certain aspects, to achieve a desired flow rate a plurality of parallel separation channels may be used in one or more acoustophoresis devices. For example, in certain aspects two or more parallel separation channels are used, including 3 or more, such as 5 or more, 8 or more, 15 or more, 25 or more, 40 or more, 60 or more, 80 or more, 100 or more, 125 or more, 150 or more, 200 or more, 300 or more, 400 or more, 500 or more, or about 500 to 1000. The separation channels may be contained on one or more chips, such as 2 or more, 5 or more, 10 or more, 20 or more, 50 or more, or about 50 to 100. Moreover, a plurality of vibration transducers may be used, such as 2 or more, 5 or more, or about 10 to 50.

Figure 5:
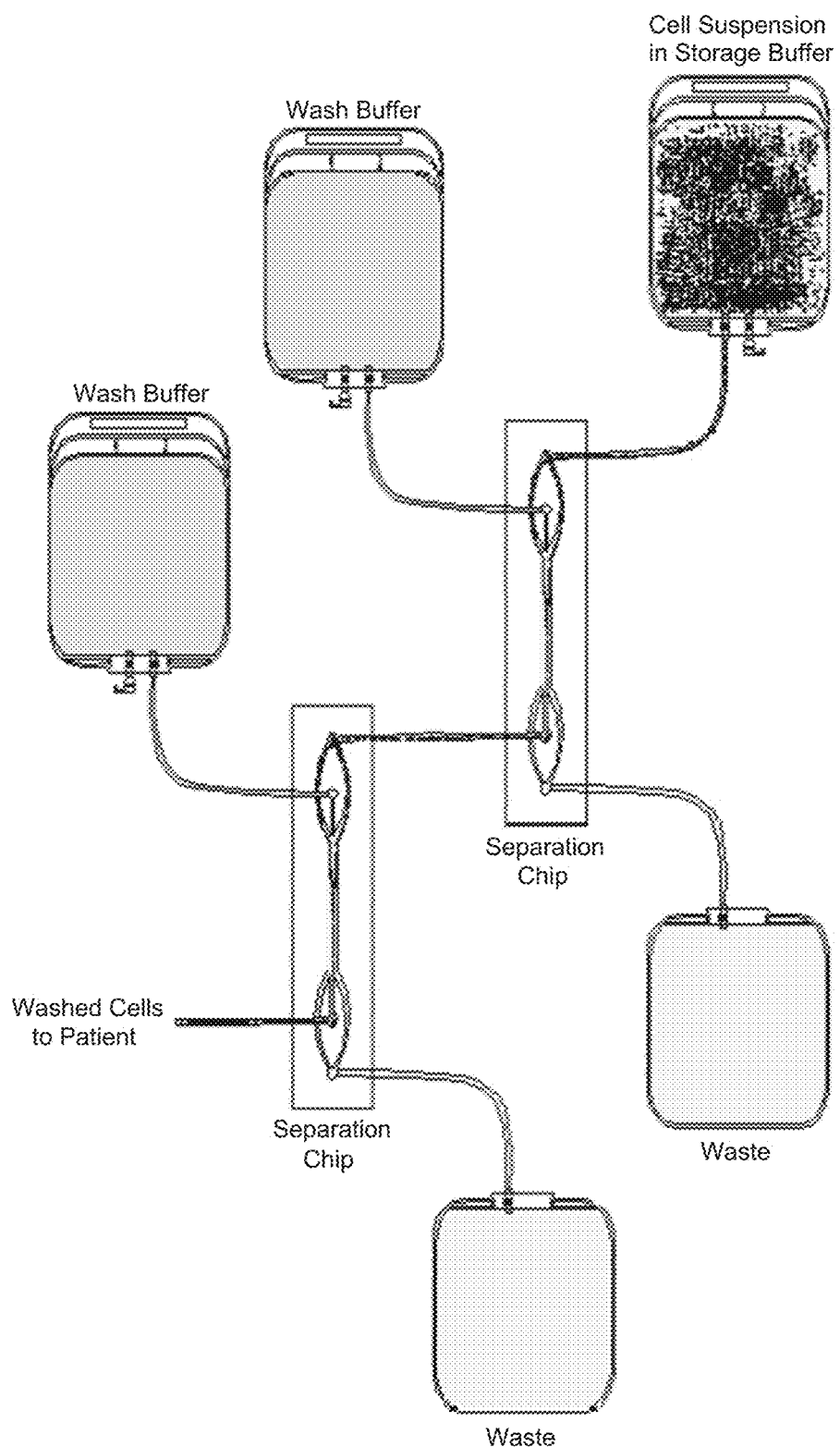
FIG. 5 provides a schematic depiction of an embodiment of the present disclosure. This embodiment is a variant of the embodiment presented in FIG. 4, wherein cells are passed through a plurality of acoustophoresis devices.

In certain aspects, two or more separation channels are arranged in series. For example, FIG. 5 presents an embodiment in which the output from one acoustophoresis device is used as an input to a second acoustophoresis device. Any convenient number of acoustophoresis devices and/or separation channels may be arranged in series and/or in parallel to facilitate the transfer of a therapeutic agent from a first medium into a second medium.

Accordingly, in some embodiments, the subject methods may involve the use of two or more acoustophoresis devices, such as 3 or more, including 4 or more, 5 or more, 6 or more, or 7 to 10. Such acoustophoresis devices may be arranged in any convenient configuration, such as in a serial configuration, parallel configuration, or a combination of the two. Moreover, the acoustophoresis devices may be substantially identical, identical, or heterogeneous (e.g., differ in one or more ways, such as in the dimensions of the flow channel, the applied voltage, the oscillation frequency, etc.).

Moreover, the acoustophoresis devices used in practicing the subject methods may in some aspects contain one or more additional components. Examples of such components include, but are not limited to, one or more valves (e.g., pinch valves, and the like), reservoirs (e.g., sample reservoirs, wash reservoirs, waste reservoirs, and the like), pumps (e.g., syringe pumps, peristaltic pumps, and the like), connective tubing (e.g., silicone tubing), housings, processors, and the like.

Administration of a Therapeutic Agent to a Subject

In certain aspects, the subject methods include administering the therapeutic agent suspended in the second (or third, fourth, fifth, etc.) medium to a subject. The methods may involve administration of a therapeutic agent to a variety of subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses.

Figure 4:
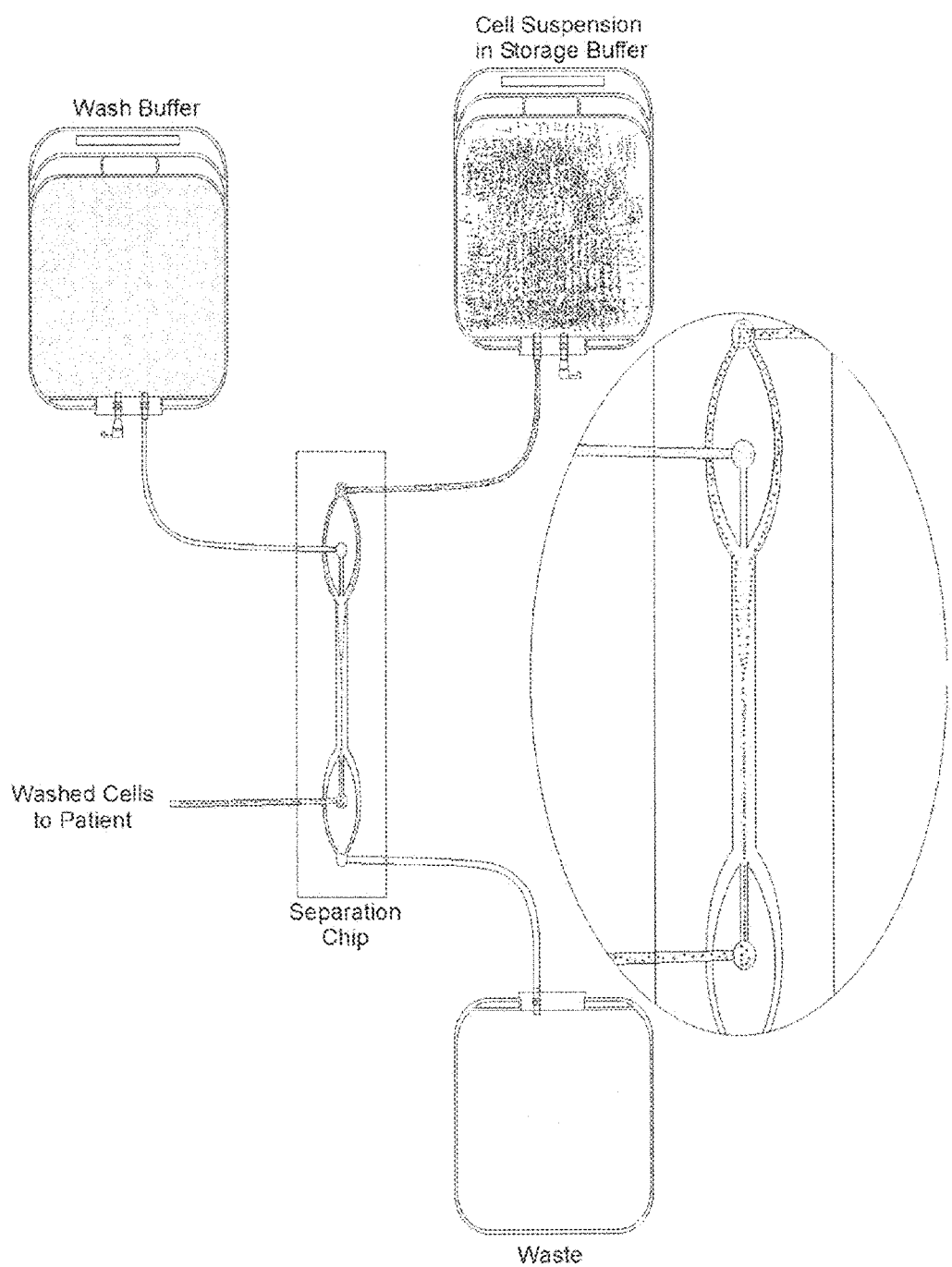
FIG. 4 provides a schematic depiction of an embodiment of the present disclosure. In this embodiment, a gravimetric fluid flow is used to pass cells through the acoustophoresis device wherein cells are transferred from a first storage medium into a second, sterile physiological medium, labeled as a wash buffer. Alternatively, a pump mechanism, such as a peristaltic pump, can be used to control the flow of the fluid through the acoustic-focusing chip and into the patient. All tubing and the acoustophoresis chip can be connected and maintained in an entirely closed, aseptic system using connectors and methods known in the art.

FIG. 4 provides a schematic depiction of such an embodiment of the present invention. In this embodiment, a gravimetric fluid flow is used to pass cells through the acoustophoresis device wherein cells are transferred from a first storage medium into a second, sterile physiological medium, labeled as a wash buffer. Alternatively, a pump mechanism, such as a peristaltic pump, can be used to control the flow of the fluid through the acoustophoresis device and into a patient. All tubing and the acoustophoresis chip can be connected and maintained in an entirely closed, aseptic system using connectors and methods known in the art.

Any convenient means of administration may be used in practicing the subject methods. Examples of routes of administration include, but are not limited to, parenteral (e.g., subcutaneous, intramuscular, intradermal, intravenous and intrathecal), intraperitoneal, intravesicular, oral, etc., administration. In certain aspects, the subject methods may be performed at a subject's bedside.

In certain aspects, the subject methods may involve allotransplantation and/or xenotransplantation. Aspects further include therapeutic agents being obtained from a subject, manipulated and/or processed in one or more ways, and re-administered to the subject.

Accordingly, in certain aspects, the subject methods are performed under sterile conditions and/or are sterile. By "sterile" is meant a sample that is free or substantially free from live bacteria or other microorganisms.

Devices

Also provided are devices for practicing the subject methods. In certain aspects, the devices may include one or more acoustophoresis devices configured to connect with one or more containers. Embodiments of the devices may include connectors configured to connect with one or more containers so as to maintain an entirely closed, aseptic system. In certain aspects, the device may be configured to connect to a container containing a sterile physiologically compatible buffer and a container containing a therapeutic agent in, e.g., storage buffer or freezing buffer.

Embodiments further include one or more one or more acoustophoresis devices in fluidic communication with a container containing a sterile physiologically compatible buffer, and configured to connect with a container containing a therapeutic agent (e.g., in storage buffer, freezing buffer, etc.). Such devices may be sterile. The devices may include connectors configured to connect with the container containing a therapeutic agent so as to maintain an entirely closed, aseptic system.

In certain aspects, the devices include a first container providing the therapeutic agent suspended in a first medium; a second container providing a second medium; an acoustophoresis device (e.g., as described above) in fluidic communication with the first and second containers and configured to exchange the second medium for the first medium, to produce the therapeutic agent suspended in the second medium.

In certain aspects, devices may include more than two containers, such as 3 or more, 4 or more, or 5 or more. The containers may contain a third medium, fourth medium, fifth medium, etc. Moreover, devices may contain 2 or more acoustophoresis devices, such as 3 or more, including 4 or more, 5 or more, 6 or more, e.g., 7 to 10. Such acoustophoresis devices may be arranged in any convenient configuration, such as in a serial configuration, parallel configuration, or a combination of the two. Moreover, the acoustophoresis devices may be substantially identical, identical, or heterogeneous (e.g., differ in one or more ways, such as in the dimensions of the flow channel, the applied voltage, the oscillation frequency, etc.). The containers and acoustophoresis devices may be fluidically coupled using tubing, connectors, and methods known in the art. The devices may be integrated into the same article of manufacture as a single unit, or distributed among two or more different units (e.g., as a system) where the two or more different units are in communication with each other, e.g., via a wired or wireless communication protocol.

Accordingly, aspects of the present disclosure further include systems, e.g., computer based systems, which are configured to transfer therapeutic agents as described above. A "computer-based system" refers to the hardware, software, and data storage devices used to analyze the information of the present invention. The minimum hardware of embodiments of the computer-based systems includes a central processing unit (CPU) (e.g., a processor), an input device, an output device, and data storage device. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing one or more tasks involved in the analysis of the magnetically labeled moieties.

In certain aspects, a system may operate in a closed-loop fashion. For example, in some embodiments a system may measure one or more parameters of the exchange of the therapeutic agent, such as the flow rate or the rate of administration of the therapeutic agent to a subject, and the like. The system may change one or more parameters of the subject acoustophoresis devices on a substantially real-time basis to automatically obtain the desired results. For example, the system may alter one or more of the flow rate of an acoustophoresis device, the frequency of the vibration generator of an acoustophoresis device, the power applied to the vibration generator, etc. In certain aspects, such a closed-loop system may involve applying one or more statistical or learning machine algorithms, such as genetic algorithms, neural networks, hidden Markov models, Bayesian networks, and the like.

Additionally, systems of the present disclosure may include a number of additional components, such as data output devices, e.g., monitors, printers, and/or speakers, data input devices, e.g., interface ports, a keyboard, a mouse, etc., fluid handling components (e.g., pumps, valves, and the like), power sources, etc.

Kits

Also provided are kits for practicing one or more embodiments of the above-described methods. The subject kits may include various components and reagents.

In some instances, the kits include one or more acoustophoresis devices configured to connect with one or more containers. The kits may include a container containing a sterile physiologically compatible buffer, and the acoustophoresis device(s) may be configured to administer therapeutic agent transferred into the physiologically compatible buffer into a subject. In some embodiments, the kits are configured to be used at a subject's bedside, e.g., using gravimetric flow and/or mechanically-assisted fluid flow (e.g., as described above)

In some instances, the kits include at least reagents finding use in the methods (e.g., as described above); and a computer readable medium having a computer program stored thereon, wherein the computer program, when loaded into a computer, operates the computer to perform acoustophoresis as described herein; and a physical substrate having an address from which to obtain the computer program.

In addition to the above components, the subject kits may further include instructions for practicing the methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, flash memory, etc., on which the information has been recorded. Yet another means that may be present is a website address which may be used via the Internet to access the information at a removed site. Any convenient means may be present in the kits.

Utility

The subject methods, devices, and kits find use in a variety of different applications where it is desirable to exchange particles (e.g., therapeutic agents, such as cells) from one liquid medium to another liquid medium.

For example, embodiments of the subject methods may facilitate the transfer of a therapeutic agent from a storage medium (e.g., a medium containing a cryoprotectant) to an infusion medium that may be administered into a subject. The exchange of the therapeutic agent from the storage medium to the infusion medium thus may prevent complications or adverse reactions in the subject from exposure to one or more components of the storage medium (e.g., the cryoprotectant). The subject devices and methods may be utilized at a subject's bedside and, in certain embodiments, may be performed under sterile conditions. Because the subject methods and devices may rely in some embodiments solely on gravimetric fluid flow, the methods and devices may be less expensive and/or easier to administer than existing technologies.

NON-LIMITING EMBODIMENTS

Non-limiting exemplary embodiments of the present disclosure are provided as follows:
1. A method of preparing a particulate infusion composition, the method comprising:
    combining a first liquid comprising a therapeutic agent in a storage medium and a second liquid infusion medium in a manner sufficient to produce a laminar flow of the first and second media; and
    acoustophoretically moving the therapeutic agent from a first liquid medium into the second liquid medium.
2. The method according to 1, wherein the method further comprises infusing the second liquid medium into a subject.
3. The method according to any of 1-2, wherein the storage medium comprises a cryoprotectant.
4. The method according to 3, wherein the cryoprotectant is DMSO or glycerol.
5. The method according to any of 2-4, wherein the method is performed at the subject's bedside.
6. The method of any of 2-5, wherein the therapeutic agent was obtained from the subject.
7. The method of any of 1-6, wherein the therapeutic agent is contained within, associated with, or coupled to a particle to facilitate acoustophoresis of the therapeutic agent.
8. The method of 7, wherein the particle is a liposome.
9. The method of 7, wherein the particle is a polymeric bead.
10. The method of any of 7-9, wherein the therapeutic agent is a drug.
11. The method of any of 7-9, wherein the therapeutic agent is a therapeutic protein.
12. The method of any of 7-9, wherein the therapeutic agent is a nucleic acid.
13. The method of any of 1-7, wherein the therapeutic agent comprises cells.
14. The method of 13, wherein the cells are peripheral blood stem cells (PBSC), umbilical cord blood cells, hematopoietic stem cells, or induced pluripotent stem cells.
15. The method of any of 1-14, wherein combining the first and second media comprises gravimetric fluid flow.
16. The method of any of 1-15, wherein combining the first and second media comprises mechanically-assisted fluid flow.
17. The method of any of 1-16, further comprising combining the second liquid medium with a third liquid medium in a manner sufficient to produce a laminar flow of the second and third media; and
    acoustophoretically moving the therapeutic agent from the second liquid medium into the third liquid medium.
18. The method of 17, comprising administering the therapeutic agent suspended in the third medium to a subject.
19. The method of 18, wherein said administering comprises parenteral, intraperitoneal, or intravesicular administration.
20. The method of any of 18-19, wherein the subject is mammalian.
21. The method of 20, wherein the subject is human.
22. The method of any of 1-21, wherein the method is sterile.
23. A device for transferring a therapeutic agent, the device comprising:
    a first container providing the therapeutic agent suspended in a first medium;
    a second container providing a second medium;
    an acoustophoresis device in fluidic communication with the first and second containers and configured to exchange the second medium for the first medium, to produce the therapeutic agent suspended in the second medium.
24. The device of 23, further comprising a channel in fluidic communication with the acoustophoresis device and configured to receive the therapeutic agent suspended in the second medium and administer the therapeutic agent suspended in the second medium to a patient.
25. The device of 23 or 24, comprising at least one pump to control a flow rate of the first medium or the second medium through the acoustophoresis device.
26. The device of any of 23-25, wherein the acoustophoresis device comprises 2 or more separation channels.
27. The device of any of 23-26, wherein the acoustophoresis device comprises 5 or more separation channels.
28. The device of any of 23-27, wherein the acoustophoresis device comprises 10 or more separation channels.
29. The device of any of 23-28, wherein the acoustophoresis device exchanges the second medium for the first medium, to produce the therapeutic agent suspended in the second medium, at a rate of about 1 μl/min or more.
30. The device of any of 23-29, wherein the acoustophoresis device exchanges the second medium for the first medium, to produce the therapeutic agent suspended in the second medium, at a rate of about 100 µl/min or more.
31. The device of any of 23-30, wherein the acoustophoresis device exchanges the second medium for the first medium, to produce the therapeutic agent suspended in the second medium, at a rate of about 1 ml/min or more.
32. The device of any of 23-31, wherein the acoustophoresis device exchanges the second medium for the first medium, to produce the therapeutic agent suspended in the second medium, at a rate of about 100 ml/min or more.
33. The device of any of 23-32, wherein the acoustophoresis device comprises a separation chip made of silicon, steel, glass, Poly(methyl methacrylate), or polycarbonate.
34. The device of any of 23-33, wherein the acoustophoresis device comprises a piezoceramic transducer.
35. The device of any of 23-34, wherein the device is sterile.
36. The device of any of 23-35, wherein the therapeutic agent was obtained from the subject.
37. The device of any of 23-36, wherein the therapeutic agent comprises cells.
38. The device of 37, wherein the cells are peripheral blood stem cells (PBSC), umbilical cord blood cells, hematopoietic stem cells, or induced pluripotent stem cells.
39. The device of any of 23-38, wherein the device comprises a processor configured to control the exchange the second medium for the first medium in the acoustophoresis device.
40. The device of 39, wherein the processor is configured to control the device under a closed-loop feedback mechanism.
41. A kit comprising:
an acoustophoresis device configured to connect with two or more containers; and
a container providing a sterile physiologically compatible buffer.
42. The kit of 41, wherein the kits is configured to be used at a subject's bedside.
43. An acoustophoresis device configured to connect with a first container comprising a therapeutic agent in a storage medium and a second container comprising infusion medium; and configured to acoustophoretically move the therapeutic agent from the medium into the infusion medium.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Acoustophoresis chips were fabricated as described in U.S. Pat. No. 6,929,750; Laurell, et al. (2007) Chem. Soc. Rev., 2007, 36, 492-506; Petersson, et al. (2005) Analytical Chemistry 77: 1216-1221; and Augustsson, et al. (2009) Lab on a Chip 9: 810-818; the disclosures of which are incorporated herein by reference.

The initial chip size was reduced about 10 fold (from about 15×75 mm to 3×35 mm) with accompanying 10× reductions in power consumption and cost, while performing equivalently to the larger precursors. That is, FACS lysed whole blood, ammonium chloride lysed whole blood, and PBMC's from BD Vacutainer® CPT™ Cell Preparation Tubes could be washed with >90% recovery of lymphocytes and 95% rejection of debris and small molecule contamination.

The acoustophoresis chip was integrated into a holder with standardized fluidic connections and shown to function correctly to 35 psi without leakage. Configuration and attachment of the PZT driver was also investigated and optimized so that the chip and driver could be integrated as a finished assembly into the flow path of a cytometer in a simple, reproducible manner.

This assembly was interfaced to a modified BD FACSCanto™ analytical cytometer. Pressure driven fluidics were developed to supply wash buffer to the chip. Use of the washer on FACS lysed blood was investigated in detail on the BD FACSCanto™ analytical cytometer by testing multiple samples on multiple days. Samples were processed in lyse-no-wash (LNW), lyse-wash (LW) and chip-wash (CW) formats. BD TruCount™ control bead recovery was used to normalize results.

WBC recovery was 104±5% for LW and 98±6% for CW relative to LNW control. WBC subpopulations appeared unchanged relative to the LNW control. Debris removal for LW and CW methods was 99.6±0.2% and 98.5±0.9% respectively. CW and LW formats completely resolved the dimly labeled B Cell population from background.

The acoustophoresis chip was also interfaced to the BD Influx™ flow cytometer and successfully used to wash PBMC samples from BD Vacutainer® CPT™ Cell Preparation Tubes. The sorter was programmed and shown to recover only lymphocytes and remove all other monocytes and BD TruCount™ control beads.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A device for transferring a therapeutic agent from a first liquid to a second liquid infusion medium, the device comprising:
   a) a first container comprising a first liquid comprising a therapeutic agent suspended in a first medium comprising a cryoprotectant agent;
   b) second container comprising a second liquid infusion medium; and
   c) an acoustophoresis device in fluidic communication with the first and second containers and configured to acoustophoretically move the therapeutic agent from the first liquid into the second liquid infusion medium, to produce the therapeutic agent suspended in the second liquid infusion medium; wherein the device is sterile.

2. The device according to claim 1, further comprising a channel in fluidic communication with the acoustophoresis device and configured to receive the therapeutic agent suspended in the second liquid infusion medium and administer the therapeutic agent suspended in the second medium to a patient.

3. The device according to claim 2, comprising at least one pump to control a flow rate of the first medium or the second medium through the acoustophoresis device.

4. The device according to claim 2, wherein the acoustophoresis device comprises 2 or more separation channels.

5. The device according to claim 1, wherein the first container comprises a freezing bag.

6. The device according to claim 1, wherein the acoustophoresis device further comprises:
   d) a channel having a central inlet configured to receive the second liquid infusion medium,
   e) two side inlets configured to receive the first liquid comprising the therapeutic agent,
   f) a central outlet configured to output a liquid comprising the therapeutic agent in the second liquid infusion medium, and
   g) a waste liquid outlet.

7. The device according to claim 1, comprising at least one pump to control a flow rate of the first liquid or the second liquid infusion medium through the acoustophoresis device.

8. The device according to claim 7, wherein the acoustophoresis device comprises 5 or more separation channels.

9. The device according to claim 8, wherein the acoustophoresis device comprises 10 or more separation channels.

10. The device according to claim 1, wherein the acoustophoresis device comprises a separation chip made of a material selected from the group consisting of silicon, steel, glass, Poly(methyl methacrylate) and polycarbonate.

11. The device according to claim 1, wherein the acoustophoresis device comprises a piezoceramic transducer.

12. The device according to claim 1, wherein the therapeutic agent comprises cells.

13. The device according to claim 12, wherein the cells are peripheral blood stem cells (PBSC), umbilical cord blood cells, hematopoietic stem cells, or induced pluripotent stem cells.

14. The device according to claim 1, wherein the device comprises a processor configured to control the movement of the therapeutic agent from the first liquid to the second liquid storage medium in the acoustophoresis device.

15. The device according to claim 14, wherein the processor is configured to control the device under a closed-loop feedback mechanism.

16. A device for transferring a therapeutic agent from a first liquid to a second liquid infusion medium, the device comprising:
   a) a freezing bag comprising the first liquid comprising the therapeutic agent suspended in a first medium comprising a cryoprotectant agent, wherein the therapeutic agent comprises cells;
   b) second container comprising the second liquid infusion medium;
   c) an acoustophoresis device in fluidic communication with the first and second containers and configured to acoustophoretically move the therapeutic agent from the first liquid into the second liquid infusion medium to produce the therapeutic agent suspended in the second liquid infusion medium; wherein the device is sterile.

17. The device according to claim 16, further comprising a channel in fluidic communication with the acoustophoresis device and configured to receive the therapeutic agent suspended in the second liquid infusion medium and administer the therapeutic agent suspended in the second medium to a patient.

18. The device according to claim 17, comprising at least one pump to control a flow rate of the first medium or the second medium through the acoustophoresis device.

19. The device according to claim 18, wherein the acoustophoresis device comprises 2 or more separation channels.

20. The device according to claim 16, wherein the device comprises a processor configured to control the movement of the therapeutic agent from the first liquid to the second liquid storage medium in the acoustophoresis device.

* * * * *